United States Patent
Selkee

(10) Patent No.: US 9,101,734 B2
(45) Date of Patent: Aug. 11, 2015

(54) FORCE-SENSING CATHETER WITH BONDED CENTER STRUT

(75) Inventor: Thomas Selkee, Claremont, CA (US)

(73) Assignee: Biosense Webster, Inc.

( * ) Notice: Subject to any disclaimer, the term of this patent is extended or adjusted under 35 U.S.C. 154(b) by 516 days.

(21) Appl. No.: 12/207,155

(22) Filed: Sep. 9, 2008

(65) Prior Publication Data

US 2010/0063478 A1    Mar. 11, 2010

(51) Int. Cl.
*A61M 25/01* (2006.01)
*A61B 5/042* (2006.01)
*A61B 18/14* (2006.01)
*A61B 19/00* (2006.01)
*A61B 17/00* (2006.01)

(52) U.S. Cl.
CPC ............ *A61M 25/0147* (2013.01); *A61B 5/042* (2013.01); *A61B 18/1492* (2013.01); *A61M 25/0136* (2013.01); *A61M 25/0144* (2013.01); *A61B 19/5244* (2013.01); *A61B 2017/003* (2013.01); *A61B 2019/464* (2013.01); *A61B 2218/002* (2013.01); *A61B 2560/0252* (2013.01); *A61B 2562/0247* (2013.01); *A61B 2562/0261* (2013.01); *A61M 25/0141* (2013.01); *A61M 2025/015* (2013.01)

(58) Field of Classification Search
CPC .................. A61B 2019/464; A61B 2019/465; A61B 2019/466; A61B 2562/0261; A61M 25/0144
USPC .......................... 600/117, 145, 146, 561, 585; 604/95.01, 95.04, 528
See application file for complete search history.

(56) References Cited

U.S. PATENT DOCUMENTS

| 3,841,150 | A |   | 10/1974 | Pearson |
|---|---|---|---|---|
| 3,971,364 | A |   | 7/1976 | Fletcher |
| 4,764,114 | A |   | 8/1988 | Jeffcoat et al. |
| 4,856,993 | A |   | 8/1989 | Maness |
| 4,930,494 | A |   | 6/1990 | Takehana et al. |
| 5,263,493 | A |   | 11/1993 | Avitall |
| 5,368,564 | A | * | 11/1994 | Savage ........................ 604/95.04 |
| 5,391,199 | A |   | 2/1995 | Ben-Haim |
| 5,462,527 | A |   | 10/1995 | Stevens-Wright et al. |

(Continued)

FOREIGN PATENT DOCUMENTS

| DE | 19750441 | 6/1999 |
|---|---|---|
| EP | 980693 A1 | 2/2000 |

(Continued)

OTHER PUBLICATIONS

EP Search Report No. EP 09 25 2143 dated Feb. 19, 2010.

(Continued)

*Primary Examiner* — Sean Dougherty
*Assistant Examiner* — Megan Leedy

(57) ABSTRACT

A force-sensing catheter for diagnosing or treating the vessels found within a body or body space includes a center strut that is bonded, preferably thermally, along its longitudinal axis with the thermoplastic tubular member within which it is housed. The tubular member preferably has three layers: an inner layer, a braided layer and an outer layer. One or more semiconductor or metallic foil strain gages are affixed to the center strut in order to provide a measure of the bending and torsional forces on the distal tip of the catheter. Temperature compensation is achieved by having a temperature sensor near the strain gages and calibrating the catheter over a range of temperatures.

36 Claims, 12 Drawing Sheets

(56) References Cited

U.S. PATENT DOCUMENTS

| | | | |
|---|---|---|---|
| 5,487,757 A * | 1/1996 | Truckai et al. | 604/264 |
| 5,499,542 A | 3/1996 | Morlan | |
| 5,542,434 A | 8/1996 | Imran et al. | |
| 5,558,091 A | 9/1996 | Acker et al. | |
| 5,563,354 A | 10/1996 | Kropp | |
| 5,662,124 A | 9/1997 | Wilk | |
| 5,673,695 A | 10/1997 | McGee et al. | |
| 5,680,860 A | 10/1997 | Imran | |
| 5,685,878 A * | 11/1997 | Falwell et al. | 606/49 |
| 5,728,149 A | 3/1998 | Laske et al. | |
| 5,769,843 A | 6/1998 | Abela | |
| 5,826,576 A * | 10/1998 | West | 600/373 |
| 5,833,608 A | 11/1998 | Acker | |
| 5,836,894 A | 11/1998 | Sarvazyan | |
| 5,860,974 A | 1/1999 | Abele | |
| 5,861,024 A | 1/1999 | Rashidi | |
| 5,902,248 A * | 5/1999 | Millar et al. | 600/485 |
| 5,916,147 A | 6/1999 | Boury | |
| 5,944,022 A | 8/1999 | Nardella | |
| 5,964,757 A | 10/1999 | Ponzi | |
| 5,974,320 A | 10/1999 | Ward | |
| 5,983,126 A | 11/1999 | Wittkampf | |
| 6,048,329 A * | 4/2000 | Thompson et al. | 604/95.04 |
| 6,063,022 A | 5/2000 | Ben-Haim | |
| 6,123,699 A | 9/2000 | Webster, Jr. | |
| 6,171,277 B1 | 1/2001 | Ponzi | |
| 6,177,792 B1 | 1/2001 | Govari et al. | |
| 6,183,463 B1 | 2/2001 | Webster, Jr. | |
| 6,198,974 B1 | 3/2001 | Webster, Jr. | |
| 6,201,387 B1 | 3/2001 | Govari | |
| 6,203,493 B1 | 3/2001 | Ben-Haim | |
| 6,216,027 B1 | 4/2001 | Willis et al. | |
| 6,226,542 B1 | 5/2001 | Reisfeld | |
| 6,239,724 B1 | 5/2001 | Doron et al. | |
| 6,241,724 B1 | 6/2001 | Fleischman et al. | |
| 6,266,551 B1 | 7/2001 | Osadchy et al. | |
| 6,272,371 B1 * | 8/2001 | Shlomo | 600/424 |
| 6,272,672 B1 | 8/2001 | Conway | |
| 6,301,496 B1 | 10/2001 | Reisfeld | |
| 6,332,089 B1 | 12/2001 | Acker et al. | |
| 6,334,837 B1 | 1/2002 | Hein | |
| 6,335,617 B1 | 1/2002 | Osadchy | |
| 6,351,549 B1 | 2/2002 | Souluer | |
| 6,398,738 B1 * | 6/2002 | Millar | 600/486 |
| 6,436,059 B1 | 8/2002 | Zanelli | |
| 6,456,864 B1 | 9/2002 | Swanson | |
| 6,551,302 B1 | 4/2003 | Rosinko | |
| 6,569,098 B2 | 5/2003 | Kawchuk | |
| 6,574,492 B1 | 6/2003 | Ben-Haim | |
| 6,584,856 B1 | 7/2003 | Biter | |
| 6,602,242 B1 | 8/2003 | Fung et al. | |
| 6,612,992 B1 * | 9/2003 | Hossack et al. | 600/467 |
| 6,618,612 B1 | 9/2003 | Acker et al. | |
| 6,690,963 B2 | 2/2004 | Ben-Haim et al. | |
| 6,695,808 B2 | 2/2004 | Tom | |
| 6,711,429 B1 | 3/2004 | Gilboa et al. | |
| 6,727,371 B2 | 4/2004 | Müller et al. | |
| 6,814,733 B2 | 11/2004 | Schwartz | |
| 6,835,173 B2 * | 12/2004 | Couvillon, Jr. | 600/146 |
| 6,892,091 B1 | 5/2005 | Ben-Haim et al. | |
| 6,915,149 B2 | 7/2005 | Ben-Haim | |
| 6,945,956 B2 * | 9/2005 | Waldhauser et al. | 604/95.01 |
| 6,964,205 B2 | 11/2005 | Papakostas | |
| 6,973,339 B2 | 12/2005 | Govari | |
| 6,997,924 B2 | 2/2006 | Schwartz | |
| 7,077,823 B2 | 7/2006 | McDaniel | |
| 7,156,816 B2 | 1/2007 | Schwartz | |
| 7,235,070 B2 | 6/2007 | Vanney | |
| 7,297,116 B2 | 11/2007 | Varghese et al. | |
| 7,306,593 B2 | 12/2007 | Keidar | |
| 7,306,599 B2 | 12/2007 | Karasawa et al. | |
| 7,311,704 B2 | 12/2007 | Paul et al. | |
| 7,397,364 B2 | 7/2008 | Govari | |
| 7,435,232 B2 | 10/2008 | Liebschner | |
| 7,465,288 B2 | 12/2008 | Dudney et al. | |
| 7,481,774 B2 * | 1/2009 | Brockway et al. | 600/561 |
| 7,536,218 B2 | 5/2009 | Govari | |
| 7,604,605 B2 | 10/2009 | Zvuloni | |
| 7,662,151 B2 * | 2/2010 | Crompton et al. | 606/41 |
| 7,681,432 B2 | 3/2010 | Hay | |
| 7,686,767 B2 | 3/2010 | Maschke | |
| 7,911,315 B2 * | 3/2011 | Bradley | 338/2 |
| 7,914,440 B2 | 3/2011 | Otawara | |
| 7,959,601 B2 | 6/2011 | McDaniel et al. | |
| 7,984,659 B2 | 7/2011 | Fujimoto et al. | |
| 8,043,216 B2 | 10/2011 | Matsumura | |
| 8,046,049 B2 | 10/2011 | Govari et al. | |
| 8,083,691 B2 | 12/2011 | Goldenberg et al. | |
| 8,137,275 B2 | 3/2012 | Fan et al. | |
| 8,374,819 B2 | 2/2013 | Govari et al. | |
| 2001/0047129 A1 | 11/2001 | Hall | |
| 2001/0047133 A1 | 11/2001 | Gilboa et al. | |
| 2002/0002329 A1 | 1/2002 | Avitall | |
| 2002/0065455 A1 | 5/2002 | Ben-Haim et al. | |
| 2002/0068866 A1 | 6/2002 | Zikorus et al. | |
| 2002/0068931 A1 | 6/2002 | Wong et al. | |
| 2002/0165461 A1 | 11/2002 | Hayzelden et al. | |
| 2002/0193781 A1 | 12/2002 | Loeb | |
| 2003/0120150 A1 | 6/2003 | Govari | |
| 2003/0120195 A1 | 6/2003 | Milo | |
| 2003/0130615 A1 | 7/2003 | Tom | |
| 2003/0158494 A1 | 8/2003 | Dahl | |
| 2003/0187389 A1 | 10/2003 | Morency et al. | |
| 2004/0049255 A1 | 3/2004 | Jain | |
| 2004/0064024 A1 | 4/2004 | Sommer | |
| 2004/0068178 A1 | 4/2004 | Govari | |
| 2004/0097806 A1 | 5/2004 | Hunter et al. | |
| 2004/0102769 A1 | 5/2004 | Schwartz | |
| 2004/0147920 A1 | 7/2004 | Keidar | |
| 2004/0244464 A1 | 12/2004 | Hajdukiewicz et al. | |
| 2004/0254458 A1 | 12/2004 | Govari | |
| 2005/0033135 A1 | 2/2005 | Govari | |
| 2005/0080429 A1 | 4/2005 | Freyman | |
| 2005/0096590 A1 | 5/2005 | Gullickson et al. | |
| 2005/0228274 A1 | 10/2005 | Boese et al. | |
| 2005/0277875 A1 | 12/2005 | Selkee | |
| 2006/0009690 A1 | 1/2006 | Fuimaono | |
| 2006/0009735 A1 | 1/2006 | Viswanathan | |
| 2006/0015096 A1 | 1/2006 | Hauck | |
| 2006/0064038 A1 | 3/2006 | Omata et al. | |
| 2006/0074297 A1 | 4/2006 | Viswanathan | |
| 2006/0173480 A1 | 8/2006 | Zhang | |
| 2006/0184106 A1 * | 8/2006 | McDaniel et al. | 604/95.04 |
| 2006/0200049 A1 | 9/2006 | Leo | |
| 2006/0247618 A1 | 11/2006 | Kaplan et al. | |
| 2007/0021742 A1 | 1/2007 | Viswanathan | |
| 2007/0060832 A1 | 3/2007 | Levin | |
| 2007/0060847 A1 | 3/2007 | Leo et al. | |
| 2007/0100332 A1 | 5/2007 | Paul et al. | |
| 2007/0106114 A1 | 5/2007 | Sugimoto et al. | |
| 2007/0106165 A1 * | 5/2007 | Tulkki | 600/486 |
| 2007/0142749 A1 | 6/2007 | Khatib et al. | |
| 2007/0151391 A1 | 7/2007 | Larkin et al. | |
| 2007/0156114 A1 * | 7/2007 | Worley et al. | 604/525 |
| 2007/0161882 A1 | 7/2007 | Pappone | |
| 2007/0167740 A1 | 7/2007 | Grunewald et al. | |
| 2007/0167818 A1 | 7/2007 | Osborn et al. | |
| 2007/0179492 A1 | 8/2007 | Pappone | |
| 2007/0185397 A1 | 8/2007 | Govari et al. | |
| 2007/0191829 A1 | 8/2007 | McGee et al. | |
| 2007/0197939 A1 | 8/2007 | Wallace et al. | |
| 2007/0233044 A1 | 10/2007 | Wallace et al. | |
| 2007/0282211 A1 | 12/2007 | Ofek et al. | |
| 2008/0009750 A1 | 1/2008 | Aeby et al. | |
| 2008/0015568 A1 | 1/2008 | Paul et al. | |
| 2008/0051704 A1 | 2/2008 | Patel et al. | |
| 2008/0065111 A1 | 3/2008 | Blumenkranz et al. | |
| 2008/0071267 A1 * | 3/2008 | Wang et al. | 606/41 |
| 2008/0077049 A1 | 3/2008 | Hirshman | |
| 2008/0146918 A1 | 6/2008 | Magnin et al. | |
| 2008/0183075 A1 | 7/2008 | Govari et al. | |
| 2008/0200843 A1 | 8/2008 | Williams et al. | |
| 2008/0249467 A1 | 10/2008 | Burnett et al. | |
| 2008/0249522 A1 | 10/2008 | Pappone et al. | |

(56) References Cited

U.S. PATENT DOCUMENTS

| | | |
|---|---|---|
| 2008/0255540 A1 | 10/2008 | Selkee |
| 2008/0269606 A1 | 10/2008 | Matsummura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari |
| 2009/0158511 A1 | 6/2009 | Maze |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein |
| 2010/0152574 A1 | 6/2010 | Erdman |
| 2010/0160770 A1 | 6/2010 | Govari et al. |
| 2010/0160778 A1 | 6/2010 | Eskandari et al. |
| 2010/0168620 A1 | 7/2010 | Klimovitch |
| 2010/0168918 A1 | 7/2010 | Zhao |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 1502555 | 2/2005 |
| EP | 1690564 B1 | 8/2006 |
| EP | 0928601 | 4/2007 |
| EP | 1897581 | 8/2007 |
| EP | 2047797 | 3/2008 |
| EP | 2127604 | 6/2008 |
| EP | 2000789 | 12/2008 |
| EP | 1586281 | 4/2009 |
| EP | 1820464 | 4/2009 |
| EP | 2171240 | 4/2009 |
| EP | 2338411 | 9/2009 |
| EP | 2338412 | 12/2009 |
| EP | 1743575 | 1/2010 |
| EP | 2196143 A1 | 6/2010 |
| EP | 2305115 A1 | 4/2011 |
| EP | 2130508 | 12/2011 |
| JP | 8243168 A | 9/1996 |
| JP | 2000126301 A | 5/2000 |
| JP | 2000508224 A | 7/2000 |
| JP | 2005040215 A | 2/2005 |
| JP | 2005237964 A | 9/2005 |
| JP | 2006255401 A | 9/2006 |
| JP | 2007181696 A | 7/2007 |
| JP | 2005345215 | 4/2010 |
| JP | 2006064465 | 6/2011 |
| WO | WO 94/17856 A1 | 8/1994 |
| WO | WO95/10326 | 4/1995 |
| WO | WO96/05768 | 2/1996 |
| WO | WO97/29678 | 8/1997 |
| WO | WO97/29709 | 8/1997 |
| WO | WO97/29710 | 8/1997 |
| WO | WO 98/29032 A | 7/1998 |
| WO | WO03/020139 | 3/2003 |
| WO | WO2006/029569 | 3/2003 |
| WO | WO2006/086152 | 8/2003 |
| WO | WO2006/092563 | 3/2006 |
| WO | WO2007/025230 | 8/2006 |
| WO | WO2007/082216 | 9/2006 |
| WO | WO 2006/135483 A2 | 12/2006 |
| WO | WO 2007/015139 A2 | 2/2007 |
| WO | WO2007/098494 | 3/2007 |
| WO | WO2009/147399 | 5/2007 |
| WO | WO 2007/076312 A2 | 7/2007 |
| WO | WO2009/085470 | 8/2007 |
| WO | WO2007/111182 | 10/2007 |
| WO | WO2007/050960 | 11/2007 |
| WO | WO2010/008975 | 12/2007 |
| WO | WO2007/067938 | 1/2008 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A1 | 7/2009 |
| WO | WO 2011/046874 A1 | 4/2011 |

OTHER PUBLICATIONS

Okumura, Y. et al. A Systematic Analysis of In Vivo Contact Forces on Virtual Catheter Tip-Tissue Surface Contact During Cardiac Mapping and Intervention. J of Cardiovasc Electrophysiol, vol. 19, pp. 632-640, Jun. 2008.

Biter, William J. et al., "Magnetic Wire Strain Sensor", 33rd International Sampe Technical Conference, Nov. 5-8, 2001, vol. 33, pp. 12-23, Seattle, WA.

Biter, William J. et al., "Magnetic Wire for Monitoring Strain in Composites", *Sensors*, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Instron Marketing Brochure, "Medical Device Testing Systems", Instron 2007 http:/ /web.archive.org/web/20080318092822/http:/ /www.instron.com.tr/wa/library/streamfile.aspx?doc=1678& downland=true.

Instron, "Series 3300 Load Frames, Reference Manual Equipment", Instron, pp. 1-5 and 1-10, 2004.

Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).

Peirs, J. et al., "Design of an Optical Force Sensor for Force Feedback during Minimally Invasive Robotic Surgery", Eurosensors XVII, 2003, pp. 1063-1066, http:/ /mech.kuleuven.be/micro/pub/medic/ Paper_Eurosensors_2003_MIS_sensorextended.pdf.

Partial European Search Report mailed on Sep. 18, 2009 from related European Patent Application No. 08253265.6.

Partial European Search Report mailed on Dec. 7, 2009 from related European Patent Application No. 09251502.2.

Partial European Search Report mailed on Mar. 29, 2010 from related European Patent Application No. 09252879.3.

(56) References Cited

OTHER PUBLICATIONS

Partial European Search Report mailed on Apr. 1, 2010 from related European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

* cited by examiner

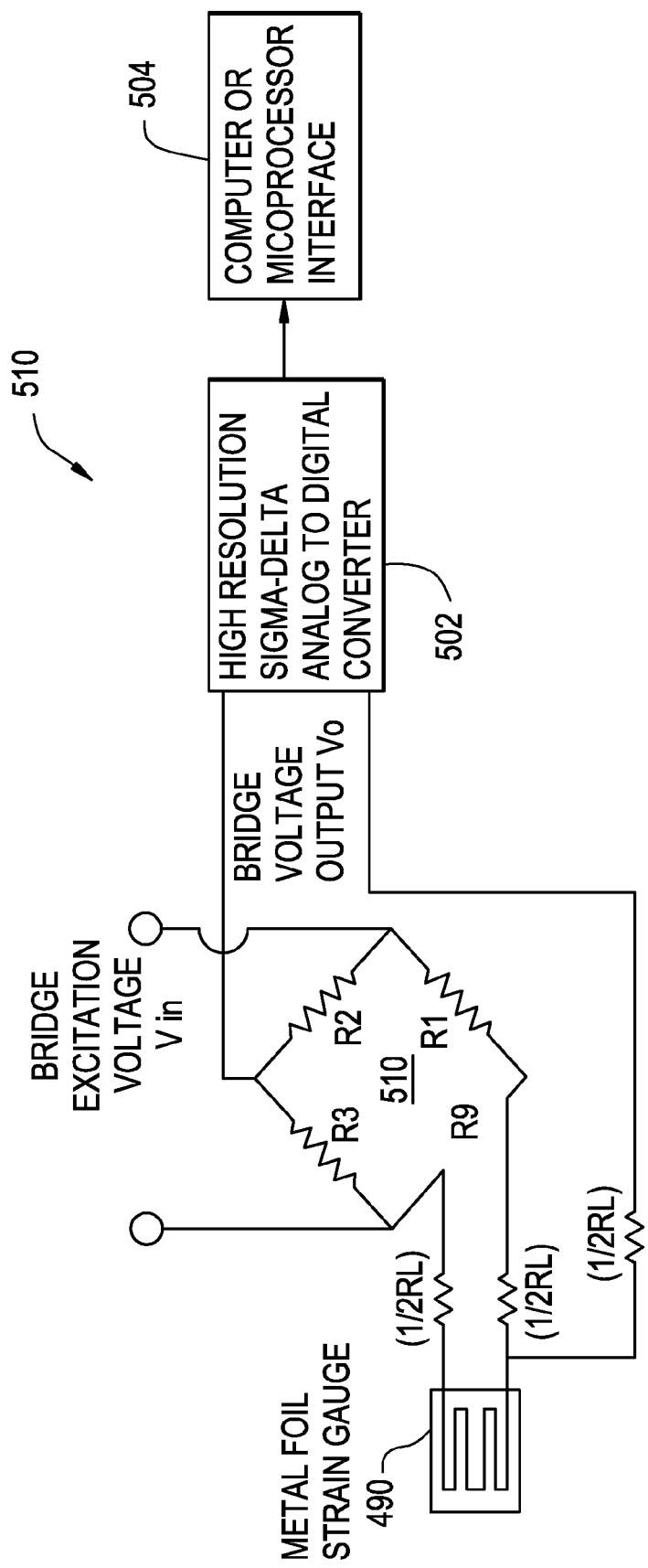

FORCE-SENSING CATHETER WITH BONDED CENTER STRUT

FIELD OF THE INVENTION

The present invention relates to a medical device for use in the vessel of a patient for the purpose of diagnosing or treating the patient, such as mapping tissue and/or ablating tissue using radio frequency (RF) or other sources of energy. More particularly, the invention relates to a catheter having a center strut bonded into the catheter tip to define an inseparable composite tip structure that maximizes the open internal volume of the catheter tip and the torsional rigidity of the catheter tip while minimizing the outside diameter of the catheter tip and providing uniform on-plane tip deflection. On the bonded center strut one or more strain gage force sensors are affixed for measuring catheter tip deflection and tip axial and side forces. The catheter may also include puller wires for deflecting the tip portion of the catheter.

BACKGROUND OF THE INVENTION

Many abnormal medical conditions in humans and other mammals have been associated with disease and other aberrations along the lining or walls that define several different body spaces. In order to treat such abnormal conditions of the body spaces, medical device technologies adapted for delivering various therapies to the body spaces using the least invasive means possible.

As used herein, the term "body space," including derivatives thereof, is intended to mean any cavity within the body which is defined at least in part by a tissue wall. For example, the cardiac chambers, the uterus, the regions of the gastrointestinal tract, and the arterial or venous vessels are all considered illustrative examples of body spaces within the intended meaning.

The term "vessel," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of vessels within the intended meaning. Blood vessels are also herein considered vessels, including regions of the vascular tree between their branch points. More particularly, the pulmonary veins are vessels within the intended meaning, including the region of the pulmonary veins between the branched portions of their ostia along a left ventricle wall, although the wall tissue defining the ostia typically presents uniquely tapered lumenal shapes.

One means of treating body spaces in a minimally invasive manner is through the use of catheters to reach internal organs and vessels within a body space. Electrode or electrophysiology (EP) catheters have been in common use in medical practice for many years. They are used to stimulate and map electrical activity in the heart and to ablate sites of aberrant electrical activity. In use, the electrode catheter is inserted into a major vein or artery, e.g., the femoral artery, and then guided into the chamber of the heart that is of concern in order to perform an ablation procedure.

U.S. Pat. No. 6,272,672 to Ben-Heim discloses the use of one or more piezoelectric elements or strain gages for generating signals indicative of bending about the axes of a catheter. While this patent discusses the use of such sensors for measuring and depicting the bend of the catheter to the user it does not provide a means for accurately providing force sensing at the tip of the catheter.

U.S. Pat. No. 6,612,992 to Rambow et al. discloses an ultrasound catheter that uses a plurality of strain gages placed along the periphery of the catheter to provide information regarding the position of the catheter in the cardiovascular system, however, there is no teaching with respect to sensing the force at the tip of the catheter.

As EP catheters are used in more procedures where tissue perforation is an issue, it would be desirable to have a tip electrode that provides more feedback such as force detection and tissue contact while having similar characteristics to existing EP catheter tips electrodes.

Furthermore, as EP catheters are used to ablate dynamically moving tissue, it will be necessary to have a catheter that accurately measures the force at the tip of the catheter while also having desirable deflection characteristics such as on-plane deflection.

SUMMARY OF THE INVENTION

The invention is directed to a catheter having integrated sensors for measuring the force on the tip of the catheter as well as providing information regarding deflection of the catheter body. The catheter of the present invention may also be readily implemented as a bidirectional steerable catheter having excellent on-plane deflection characteristics. The catheter comprises an elongated, tubular catheter body having at least one lumen extending therethrough and a deflectable tubular tip section having a center strut and two half-cylindrical lumens extending therethrough. The center strut is bonded, preferably thermally, to the interior of the tubular catheter substantially along the entire length of the center strut thereby creating an inseparable tip structure. One or more strain gages are affixed to the center strut to provide the system with information on the tip force and deflection of the catheter body.

The strain gages are affixed to the bonded central strut in distinct orientations. Bending strain is detected by the strain sensor affixed in parallel to the longitudinal axis of the strut. Torsional strain is detected by the two stain sensors oriented at 90 degrees to each other and at forty-five degrees with respect to the longitudinal axis of the strut. Because both bending and torsional strains of the bonded center strut are monitored and the strut is bonded along its longitudinal edge to the inner diameter of the elongate tubular member, forces applied to the outer diameter of the catheter tip can be determined. For added sensitivity, at the location of the torsional deflection sensors the center strut may be "necked down" or slotted to provide a means of amplifying the sensed strain. The strain gage may be either a silicon based strain gage or a metallic foil strain gage. Circuitry for determining strain based on the resistance seen at the strain gage resides in the handle of the catheter and/or the navigation or ablation system to which the catheter is connected. Most metallic strain gage alloys exhibit a nearly linear gage factor variation over a broad temperature range which is less than ±1% within ±100° C. In two-wire installations, the error introduced by lead-wire resistance is a function of the resistance ratio R1/Rg. The lead-wire error is usually not significant if the lead-wire resistance (R1) is small in comparison to the gage resistance (Rg), but if the lead-wire resistance exceeds 0.1% lead-wire temperature compensation should be provided for improved measurement accuracy. Temperature compensation is required for silicon based strain gages. Temperature compensation can be based on the temperature sensors which are used as a means of feedback control in ablation catheters.

The catheter further comprises first and second puller wires having proximal and distal ends. Each puller wire extends from a control handle at the proximal end of the catheter body through a lumen in the catheter body and into one of the lumens in the tip section. The puller wires may be disposed in a tubular sleeve dimensioned so as to maintain the puller wires in close adjacent relationship. The distal ends of the puller wires are fixedly attached either to opposite sides of the center strut, to the tip electrode or the tubular structure of the distal tip section of the catheter.

The control handle includes a steering assembly having a lever arm carrying a pair of pulleys for drawing corresponding puller wires to deflect the tip section of the catheter. The pulleys are rotatably mounted on opposing portions of the lever arm such that one pulley is moved distally as the other pulley is moved proximally when the lever arm is rotated. Because each puller wire is trained on a respective pulley, rotation of the lever arm causes the pulley that is moved proximally to draw its puller wire to deflect the tip section in the direction of the off-axis lumen in which that puller wire extends.

Specifically, the present invention is a composite catheter tip comprising an extruded thin walled elastomeric tube spirally wrapped with a reinforcing braid wherein the elastomeric tube that has a center strut comprised of a thin elongated rectangular metallic strip where both thin longitudinal sides (edges) of the said strip are bonded, preferably thermally, to the inside wall of the elastomeric tube thereby creating a composite structure with inseparable members. The term "inseparable" is used to denote the creation of a composite structure between the elastomeric tube and the metallic strip so that any attempt to separate the elastomeric tube and metallic strip would cause irreversible destruction of the composite structure.

This composite tip structure provides two enclosed, large diametrically-opposed, half moon shaped lumens extending through the tip providing space for wiring, sensors, fluid carrying tubing and the like. The strut separating the half moon shaped lumens can be constructed from any of a number of superelastic (metallic) alloys such as nitinol, beta titanium or spring tempered stainless steel. This composite catheter tip design maximizes the cross-sectional area of the open lumens in the catheter tip and torsional rigidity of the catheter tip while minimizing the outer diameter of the catheter tip by providing a single uniform area moment of inertia at any cross section of the catheter tip the longitudinal axis because the bonded center strut and elastomeric tube are not allowed to move with respect to each other during tip deflection. This composite structure provides uniform on-plane tip deflection and uniform torque and deflection forces regardless of the tip deflection angle because the tip cross-sectional area moment of inertia remains constant along the entire tip length during tip deflection. All known prior art tip designs exhibit varying cross-sectional area moments of inertia during tip deflection because the inner strut and outer elastomeric tube are fixed to each other only at their proximal and distal end locations and the strut and outer tube move with respect to each (other) during tip deflection. In all prior art designs, the combined centroidal axis of the independently moving strut and outer tube is continuously variable during tip curvature since the absolute distance between the centroidal axis of the whole (strut and outer tube) and the centroidal axis of each of the parts is variable. This produces non-uniform torque and deflection forces that are dependent on the degree of tip curvature.

The deflection curve profile of the catheter tip can be modified by varying the area moment of inertia of the strut cross section perpendicular to the struts longitudinal axis by utilizing cutting or coining operations that either remove material or change the material thickness in various portions of the center strut cross section. The composite deflecting tip with a bonded center strut has a large width to thickness ratio thus providing a first centroidal axis that has a large area moment of inertia and a second corresponding low area moment of inertia about a centroidal axis orthogonal to the first centroidal axis thereby providing exceptional on-plane deflection characteristics.

The present invention provides a single unified high-performance composite structure for the deflecting tip assembly of a deflectable catheter that combines the properties of elastomers and metals and eliminates extruded core lumens. The two half-cylindrical lumens created by the bonded strut provide a large volume in which to place wiring, tip force and location sensors and tip irrigation lumens. Alternatively, an intermediate portion between the deflectable tip section and the tip electrode can be provided in which there is no center strut and which provides even greater room for temperature and location sensors. Catheter tip diameters can be reduced since the working volume of the tip lumen is maximized with this design.

In a preferred embodiment of the catheter an elongate tubular member having a proximal end and a distal end and having a lumen is thermally bonded to the longitudinal edges of a center strut that extends in the deflectable portion of the catheter. This bonding creates an inseparable composite structure from the elongate tubular member and the center strut.

A tip electrode is disposed at the distal end of the tubular member. A molded coupling has a distal portion adapted to receive a portion of the proximal end of the tip electrode and a proximal portion having at least one slot adapted to receive at least one of the first or second longitudinal edges of the center strut.

The distal end of the center strut comprises at least one snap-fit notch and the molded coupling further comprises at least one snap-fit wedge adapted to receive the snap-fit notch. This construction enables the rapid assembly of the tip electrode and the composite tubular member and center strut.

BRIEF DESCRIPTION OF THE DRAWINGS

FIG. 15 depicts a schematic for the force measurement circuitry for use in a deflectable catheter having a metallic foil strain gage sensor in accordance with the present invention.

DETAILED DESCRIPTION OF THE INVENTION

Figure 1A:
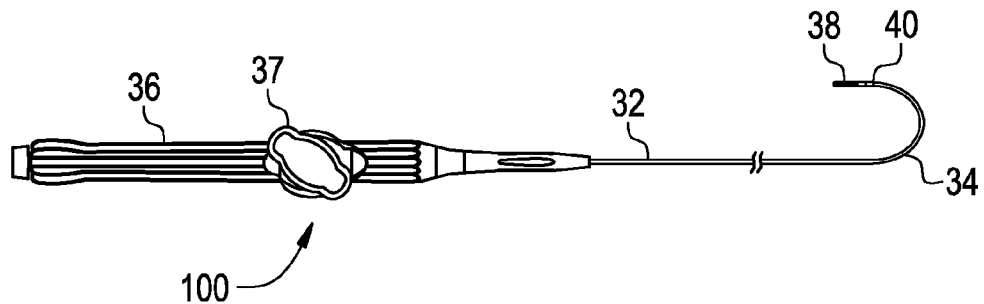
FIGS. 1A-C are a planar views of a deflectable EP catheter with rocker type deflection control handle in accordance with the present invention.
Figure 1B:
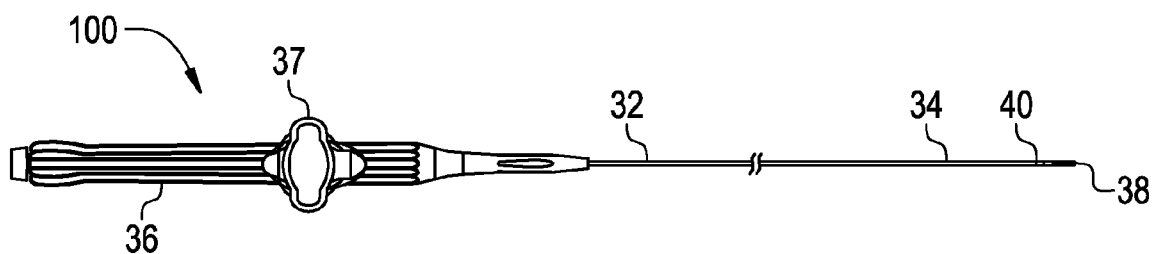
Figure 1C:
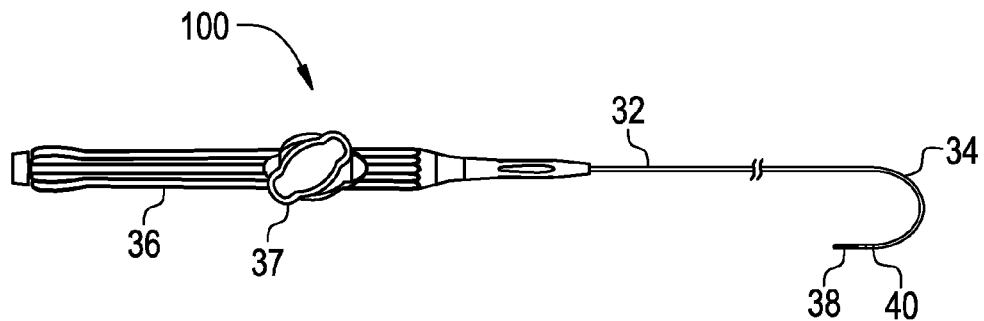
Figure 1D:
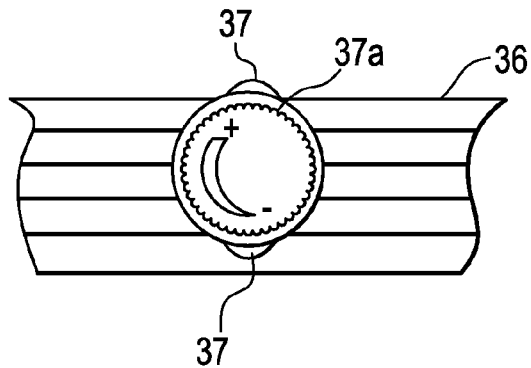
FIG. 1D is a planar view of the friction control knob located on the rocker type deflection control handle.

FIGS. 1A-C depict a planar view of an embodiment of a deflectable catheter in accordance with the present invention. As shown in FIG. 1B, a preferred catheter 100 comprises an elongated tubular catheter body having a proximal section 32, a distal tip section 34 and a control handle 36 at the proximal end of the proximal section 32. Tip electrode 38 and optional ring electrode 40 are placed at or near deflectable distal tip section 34 so as to provide a source of ablation energy if the desired device is an RF ablation catheter or for receiving electrical signals if the catheter is a diagnostic EP mapping catheter. Control handle 36 may be one of many designs capable of placing a pulling force on puller wires used to deflect the deflectable tip section 34. Preferably, control handle 36 is the handle used in the Biosense EZ-Steer bidirectional family of products which control handle is depicted in FIGS. 1A-C. The "rocker" type lever 37 pulls one of two puller wires to deflect the catheter tip in one direction (FIG. 1A) then can alternatively select the second (opposite) puller wire to deflect the catheter tip in the other direction (FIG. 1C). The control handle 36 also had an adjustable friction control knob 37a shown in FIG. 1D that allows the operator to use the rocker lever 37 in a free state or to adjust the tension to lock the rocker level 37 and the deflected tip in place. The amount of friction in the movement of the rocker lever 37 increases as the friction control knob 37a is rotated clockwise until it reaches the fully locked position.

Figure 2:
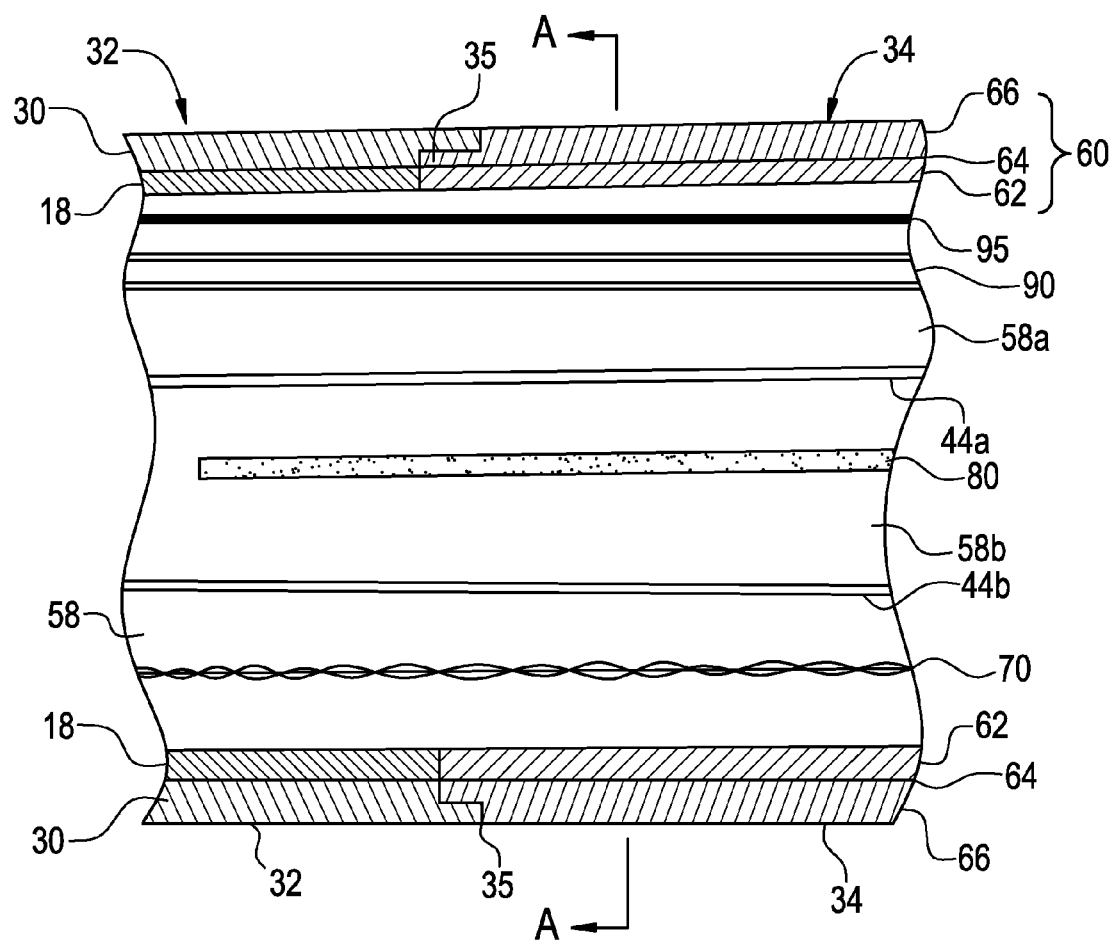
FIG. 2 is a longitudinal cross-sectional view of the deflectable distal tip section and a portion of the proximal section of the catheter of FIG. 1 including strain gage force sensors on the bonded center strut.
Figure 3:
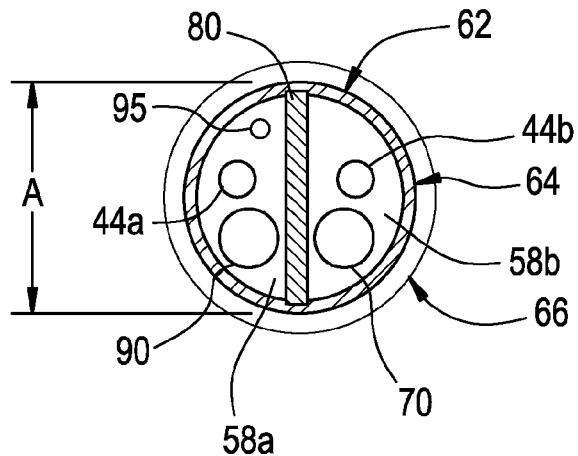
FIG. 3 is a cross-sectional view of the tubular section of the EP catheter of FIG. 2 through line A-A.

FIG. 2 depicts a cross-sectional view of the transition from proximal section 32 and deflectable distal section 34 of catheter 100 taken perpendicular to the center strut 80 that forms a portion of the catheter and FIG. 3 depicts the cross-section of the catheter of FIG. 2 through line A-A. Catheter 100 comprises an elongated tubular construction having a central lumen 58 through the distal portion 34 and two half-cylindrical lumens 58a and 58b in the deflectable tip portion 34. The proximal section 32 is flexible but substantially non-compressible along its length. Proximal section 32 can be made of any suitable construction and made of any suitable material. The preferred construction comprises an outer wall 30 made of Pellethane or PEBAX and an optional inner wall 18. The outer wall 30 may also comprise an imbedded braided mesh of stainless steel or similar material to increase torsional stiffness so that when control handle 36 is rotated the distal send of proximal section 32 as well as the distal section 34 will rotate in a corresponding manner.

The overall length of the length of the catheter will vary according to its application for use but a preferred length is between approximately 90 and 120 cm and more preferably between approximately 100 and 110 cm. The outer diameter of the proximal section 32 is also a design characteristic that varies according to the application of the catheter but is preferably less than approximately 8 French (Fr). Optional inner wall 18 comprises a polymeric tube which may optionally be spirally-sliced and is sized so that the outer diameter is about the same size or slightly smaller than the inner diameter of outer wall 30 thereby providing additional stiffness which can be controlled by the pitch angle of the spiral slice.

In the embodiment shown, the distal section 34 and the proximal section 32 are separate structures that have been fixedly attached to each other. Proximal section 32 and distal section 34 may be attached using a polyurethane adhesive at the joint 35 between the two sections. Other means of attachment include joining the proximal and distal sections using heat to fuse the sections together.

In the EP catheter of the present invention, tip electrode 38 and optional ring electrodes 40 shown in FIGS. 1A-1C are each electrically connected to one of the bundle of lead wires 70. Each wire in the bundle of lead wire 70 extends from the control handle 36 through the lumen 58 in the proximal section 32 and through one of lumens 58a or 58b in distal section 34 to tip electrode 38 and optional ring electrode (or electrodes) 40. The proximal end of each lead wire 70 is connected to an appropriate connector (not shown) in the control handle 36 which can be connected to a suitable source of RF energy or to an EP mapping or other diagnostic or therapeutic system.

Figure 4:
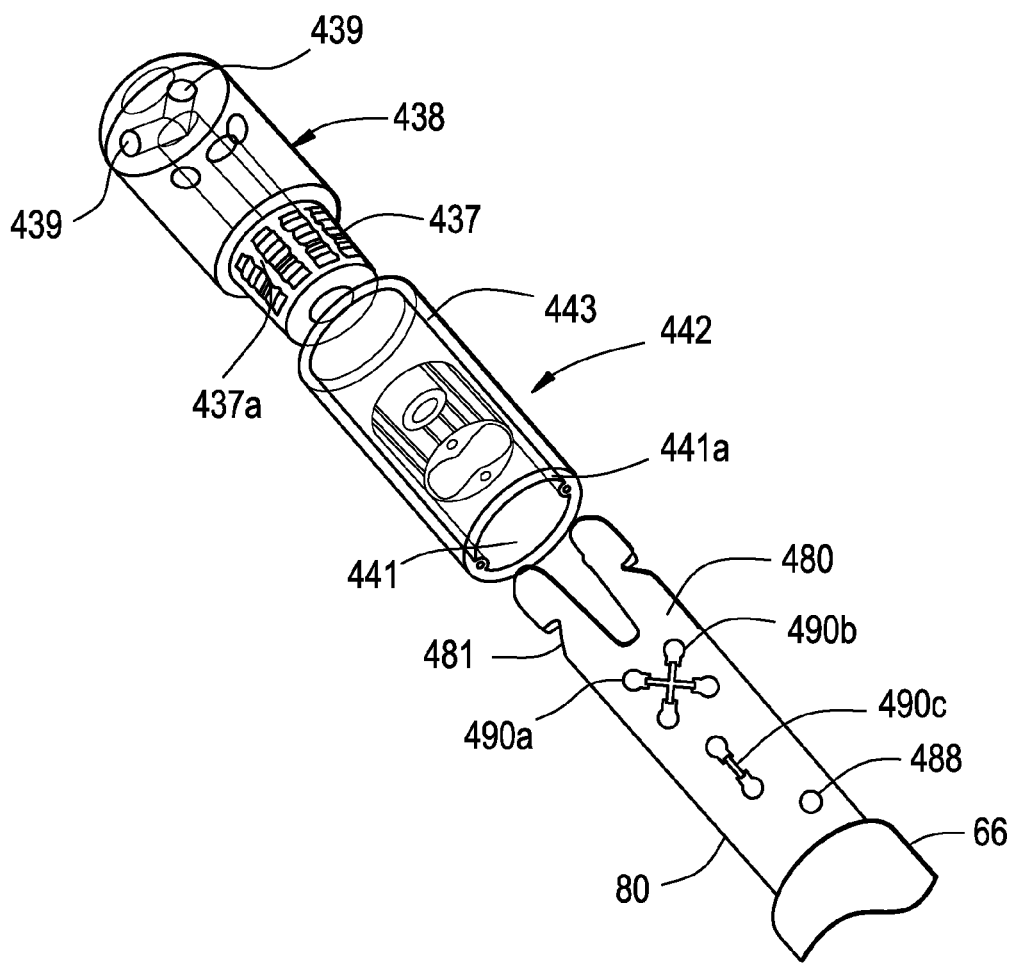
FIG. 4 is an exploded perspective view of the distal tip of an embodiment of a deflectable catheter in accordance with the present invention.
Figure 5:
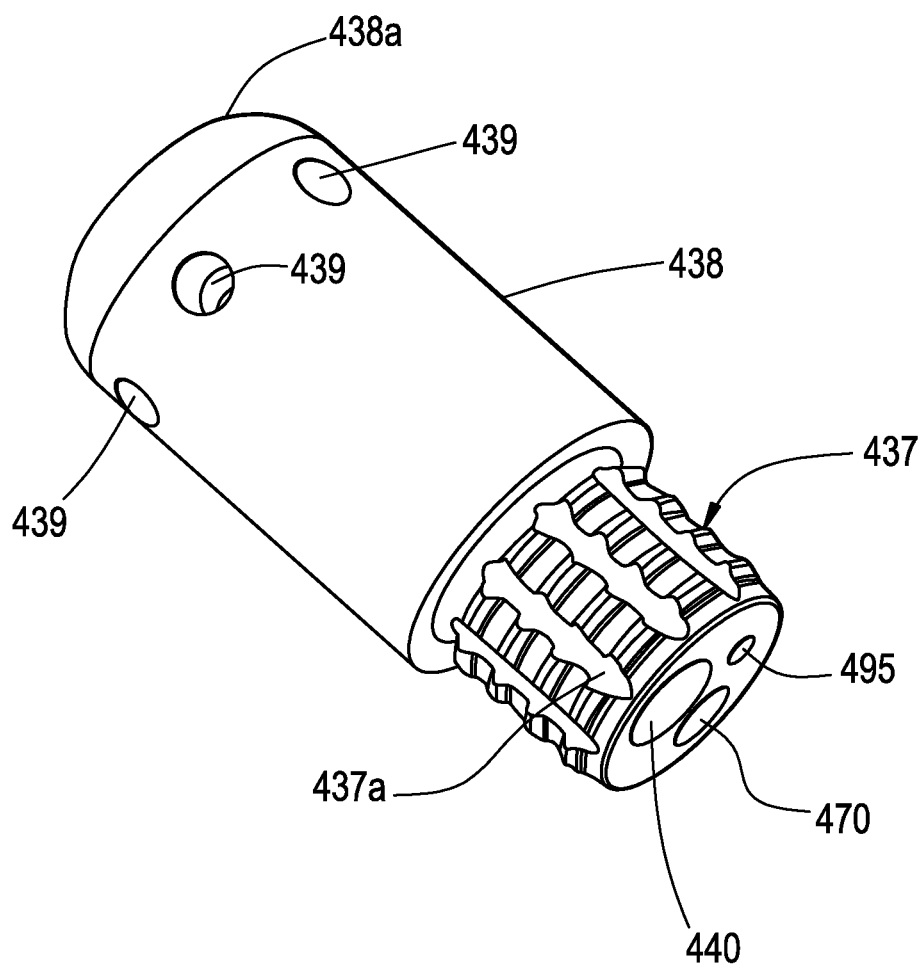
FIG. 5 is a perspective view of a tip electrode of the deflectable tip section of a catheter in accordance with the present invention.

Irrigation lumen 90 provides a conduit for transporting fluid from the proximal end of the catheter to the distal tip portion 34. Irrigation lumen 90 is in fluid communication with one or more fluid ports in the tip electrode 38. FIGS. 4 and 5 depict on possible arrangement of irrigation fluid ports 439 in a tip electrode. Irrigation lumen 90 is used to transport an irrigation fluid through the catheter and out through the fluid ports in the tip in order to reduce coagulation of bodily fluids such as blood at or near the tip electrode.

In a bi-directional catheter a pair of puller wires 44a and 44b extend through the through lumen 58 in the proximal section 32 and each extend through one of lumens 58a and 58b in distal section 34. The puller wires are made of any suitable material such as stainless steel or Nitinol wire or a non-metallic yarn such as Vectran® material. Preferably, each puller wire 44 is covered with a lubricious coating such as PTFE or a similar material. Each puller wire 44 extends from the control handle 36 to near the tip of distal section 34.

A sleeve or sleeves (not shown) may be used to house the puller wires proximally to the soft tip of the catheter. The sleeve is used to keep each puller wire on its respective sides of the center strut. For bi-directional deflection the opposing puller wires will always be placed in a separate lumen. With this design placing multiple puller wires in one lumen would be used for achieving different deflection curves in one deflection direction. Such a sleeve may be made of any suitable material, e.g., polyamide or polyurethane.

Examples of other suitable control handles 36 that can be used with the present invention are described in U.S. Pat. Nos.

6,123,699, 6,171,277, 6,183,463 and 6,198,974 the disclosures of which are hereby incorporated by reference. In such control handles proximal movement of the thumb control relative to the handle housing results in proximal movement of the first piston and first puller wire relative to the handle housing and catheter body, which results in deflection of the tip section in the direction of the lumen into which the first puller wire extends. Distal movement of the thumb control relative to the handle housing results in distal movement of the first piston, causing proximal movement of the second piston and puller wire relative to the handle housing and catheter body, which results in deflection of the tip section in the direction of the lumen into which the second puller wire extends. Additional configurations of puller wires 44 and gearing within the control handle may be used such as those disclosed in U.S. Pat. No. 7,077,823 which is also hereby incorporated by reference.

The distal section 34 is comprised of an inner layer 62, braid layer 64 and outer layer 66 of the distal tip section. The inner layer 62 of the distal section 34 of a catheter in is a thin layer of a thermoplastic elastomeric material, preferably between 0.0025-0.0035 inch in thickness. The inner layer 62 is a synthetic fiber braid layer 64 of approximately 0.002 to 0.003 inches in diameter. In a preferred embodiment the synthetic fiber is Pen monofilament from Biogeneral Advanced Fiber Technology. Outer layer 66 is an elastomeric material extruded over the braided inner layer. The inner layer 62 and the outer layer 66 may be made from elastomers having the same shore hardness or from materials having different shore hardnesses. Preferably, the elastomer is PEBAX or Pellethane due to processability and high heat deflection temperatures.

Additionally, a safety wire 95 may be used to secure the tip electrode to the catheter shaft so as to prevent detachment of the tip electrode. The safety wire is preferably a 0.0065 inch monel which is routed through the lumen 58 in the proximal portion 32 of the catheter as well as through one of the two lumens 58a or 58b in the distal tip portion 34. The distal end of the safety wire is attached to the tip electrode 38 while the proximal portion is attached to an anchor point inside the control handle 36.

FIG. 4 depicts an exploded view of the distal tip of a deflectable catheter in accordance with the present invention. FIG. 5 is a perspective view of tip electrode 438. Tip electrode 438 depicted in FIGS. 4 and 5 is a machined metallic electrode comprised of a metal that is non-reactive in bodily fluid such as of gold, platinum, palladium or an alloy thereof. Tip electrode 438 may also be made of a first metal such as copper, silver, gold, aluminum, beryllium, bronze, palladium or alloys thereof which is then plated either internally and/or externally with a non-reactive metal such as gold, platinum, palladium or an alloy thereof. Tip electrode 438 may include a plurality of irrigation ports 439 connected to a central irrigation lumen 440 although such ports and lumens are optional. The proximal end of tip electrode 438 comprises a base 437 having a smaller diameter than the remainder of the tip electrode and adapted to fit coupling 442. Base 437 may include a plurality of serrations 437a that improve the bonding of tip electrode 438 into coupling 442. Base 437 of the tip electrode 438 is heat bonded or ultrasonically welded to the coupling 442. Tip dome 438a may be machined to provide a rounded atraumatic distal tip in order to reduce tissue damage during placement and/or use of the catheter. Lumen 495 provides a passageway for safety wire 95 and lumen 470 provides a passageway for lead wire 70 that provide energy to the tip electrode 438. Lead wire 70 is attached to tip electrode 438 using a conductive solder or epoxy.

Figure 6:
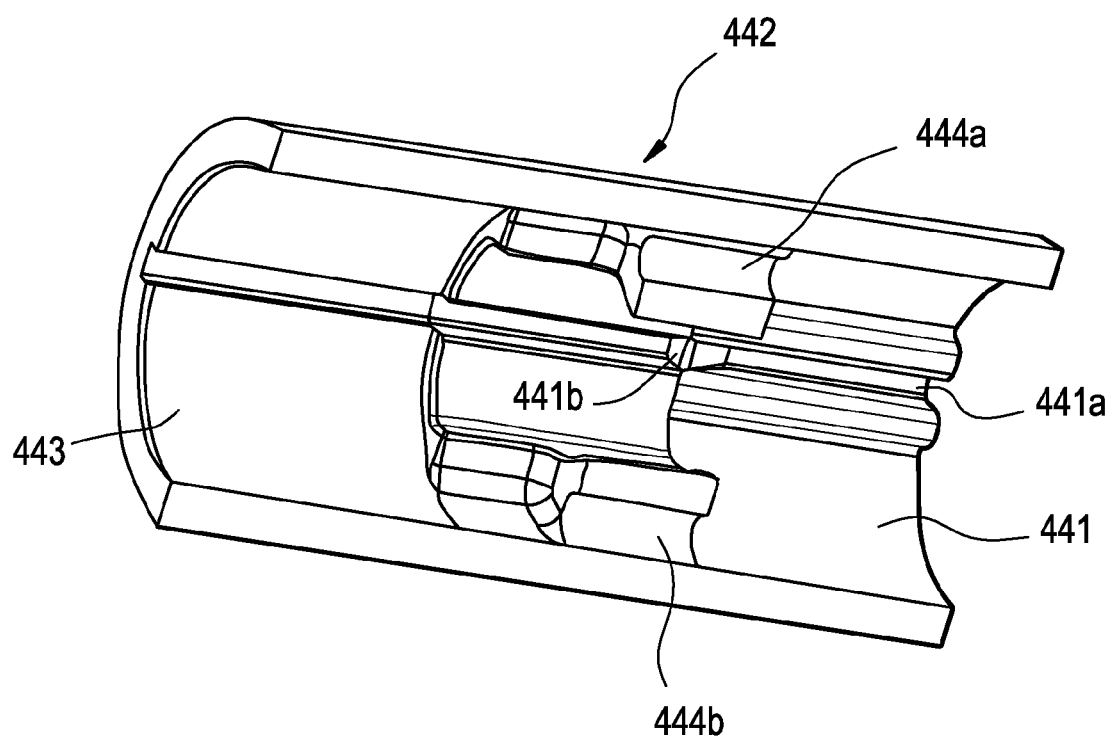
FIG. 6 is a cross-sectional perspective view of a molded coupling of the deflectable tip section of a catheter in accordance with the present invention.
Figure 7A:
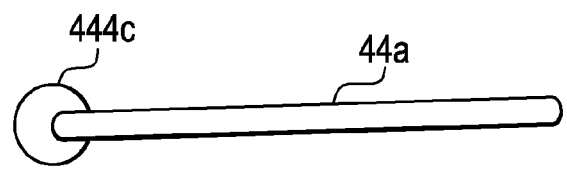
FIG. 7a is a planar view of a puller wire for use in the deflectable tip section of a catheter in accordance with the present invention.

Injection molded coupling 442 depicted in FIGS. 4 and 6 has a distal section 443 with an internal diameter at its distal end adapted to receive the base 437 of tip electrode 438 and has a proximal section 441 with a slot 441a adapted to receive the distal end 480 of the center strut 80. Coupling 442 is injection molded from a medical grade polymer such as PEEK, ABS or Polycarbonate or other appropriate material known to one skilled in the art. Distal end 480 of center strut 80 also includes a snap-fit notch 481 adapted to lock over snap-fit wedge 441b in the coupling 442 thereby providing an mechanism for the quick assembly of the distal section of the deflectable catheter which method is described in greater detail below. Puller wire anchor holes 444a and 444b are lumens that are adapted to receive puller wires 44a and 44b. Puller wires adapted for this use are shown in FIG. 7A. Puller wires 44a and 44b for use in this embodiment are preferably made of Vectran® wire which has had a ball of epoxy 444c attached to its distal end. The Vectran® wire should be cleaned with alcohol and/or an ultrasonic bath before application of a ball of epoxy that is then cured under ultraviolet light. It is important that the epoxy be well fixed to the distal end of the puller wires 44a and 44b. Alternatively, the puller wire could be high strength stainless steel (304V) to which a ball is produced at one end using a high-speed laser melting process.

Figure 12:
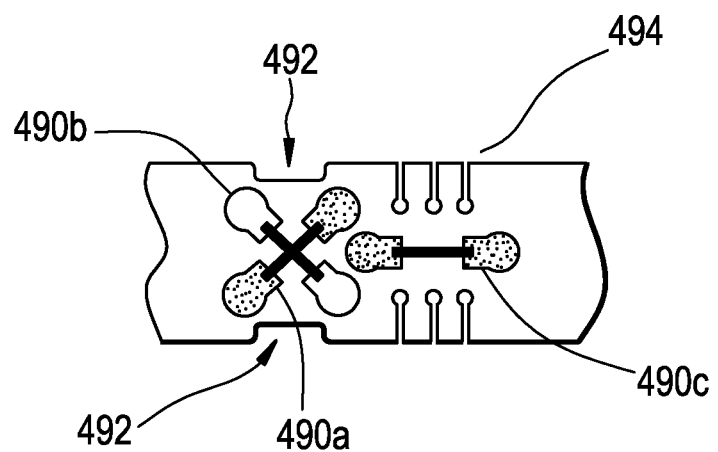
FIG. 12 is a planar view of a portion of the bonded center strut having the strain gage force sensors mounted thereon.

Near the distal end 480 of center strut 80 are mounted one or more strain gages 490a-c. The strain gages are affixed to the bonded central strut in distinct orientations. Bending strain is detected by the strain gage 490c affixed in parallel to the longitudinal axis of the strut. Torsional strain is detected by the two stain sensors 490a and 490b oriented at 90 degrees to each other and at forty-five degrees with respect to the longitudinal axis of the strut. Because both bending and torsional strains of the bonded center strut are monitored and the strut is bonded along its longitudinal edge to the inner diameter of the elongate tubular member, forces applied to the outer diameter of the catheter tip can be determined. For added sensitivity, at the location of the torsional strain gages 490a and 490b the center strut may be "necked down" by removing portions 492 from the edge of the center strut 80 as depicted in FIG. 12. Likewise, sensitivity for the bending strain may be amplified by cutting one or more slots 494 into center strut 80. Alternatively, a double set of strain gages located on opposite sides of the center strut may be used with one in compression and the other in tension. A hole 488 (FIG. 4) is punched through center strut 80 for wires to pass through for wiring the double set of strain gages on opposite sides of the center strut 80 to create a series half-bridge strain gage configuration. In this arrangement, the bridge output for the same strain can be effectively doubled. In installations where all of the bridge arms are connected to strain gages, temperature compensation is automatic, as resistance changes due to temperature variations will be the same for all arms of the bridge.

Figure 13:
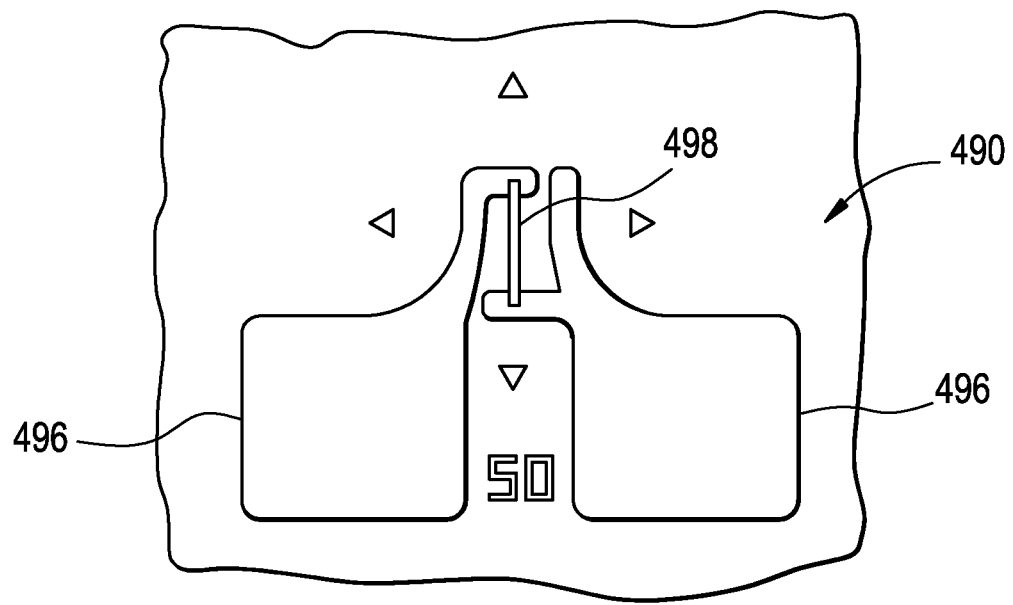
FIG. 13 is a planar view of a strain gage force sensor for use in the catheter of the present invention.

FIG. 13 depicts a typical strain sensor for use in the present invention. The preferred strain gage 490 is a rectangular single-crystal or polycrystalline silicon member aligned to the direction of the measured strain. The lead wire attachment pads 496 on either side of the sensing member 498 are designed with a symmetrical, low-stress geometry to minimize the residual stress effects on the silicon bar. They can be either conventional solder pads or wire bond pads. An aluminum surface is typically used for wire bonding and a gold-plated nickel surface for soldering. Because they are the largest feature of the strain gage device the pads determine the size of the device and the total device can be sized down to fractions of a square millimeter. A rugged, low-stress polymide backing similar to Kapton tape supports the entire structure whose total thickness is typically less than 1 mil. Because the element and the pad structure are foil thin the entire strain gage has a bend radius of less than 0.06 inch.

Lead wires preferably comprise a miniature shielded cable comprised of three inner twisted pair No. 38-48 (copper) average wire gage (AWG) double insulated poly nylon covered conductors covered with a shield and then a FEP jacket overlay. Since there are a minimum of three strain gages requiring a minimum two wires each (three wires for foil gage temperature compensation), there six total wires would be required in this embodiment. If temperature compensation at the strain gage location is utilized, at least two more wires would be required for temperature sensing using a thermocouple or thermister.

The center strut 80 is comprised of a rectangular beam section thus simple beam bending along its longitudinal axis is easy to define, but complicated deformation is induced with the addition of torsional deflection of the center strut which is a superposition of the combined stresses and variations in the tip force vectors make this a complex problem. Strain is defined as the amount of deformation per unit length of an object when a load is applied. Bending strain (moment strain) is calculated by determining the relationship between the tip curve deflection and the amount of bending which results from it. Torsional strain is measured when twisting of the catheter tip during side deflection produces a twisting strain component. Torsional strain is calculated by dividing the torsional stress by the modulus of elasticity.

The three main factors influencing the election of the strain sensor are operating temperature, strain state (gradient, magnitude, and time dependence) and required system stability. An ideal strain sensor would change resistance only due to the deformations of the center strut member, but temperature, material properties, the adhesive used to bond the sensor to the surface of the center strut and the stability of the strut member all affect the measured resistance. The two types of strain gages (semiconductor and metal based foil) could be used for sensing the center strut deflection characteristics but semiconductor sensors are the preferred type. Semiconductor sensors are more elastic than metallic foil sensors and therefore have a high propensity to return to their unstrained shape. Semiconductor sensors have a gage factor of fifty times and a sensitivity of more than 100 times (30-120) compared to metallic foil sensors which have significantly lower gage factors and sensitivity. Semiconductor sensors come in a much smaller package size at a much lower cost than for metallic foil sensors. For semiconductor sensors the resistance-to-strain relationship is nonlinear varying by 10-20% from a straight-line equation, but this is known in advance and can be compensated for mathematically. Lead wires for semiconductor based strain gages are very small and are connected to the gage by conductive epoxy, wire bonding, laser soldering/welding or ultrasonic means.

Because the center strut member is bonded along its longitudinal edge to a braided catheter tip, the sensor calibration must be performed on each semi-finished or finished catheter at the catheters operational temperature (i.e., body temperature). Manufacturing variables such as variations in the catheter shaft material properties (elastic and torsional modulus), braid pitch variation, braid diameter and tip material dimensional tolerances necessitate this requirement. Strain sensor calibration data for each catheter can be stored in an EEPROM or other storage means in the handle of the catheter so as to provide easy access to the necessary operational information. Dynamically monitoring and recording strain sensor outputs, catheter puller wire tension force and tip location as the catheter tip is deflected at different angles while exposed to different tip loading force vectors is required. Utilizing flexible catheter tip materials such as PEBAX or Arnitel® (thermoplastic copolyester based elastomer) that have a stable and flat modulus at catheter operation temperatures will increase contact force measurement accuracy.

Figure 8:
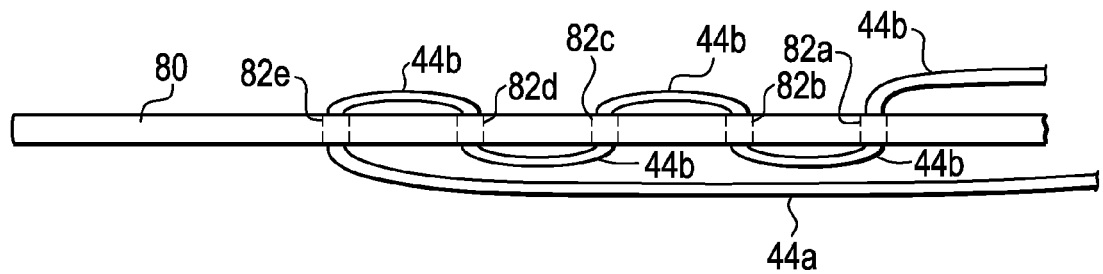
FIG. 8 is an elevational view of a center strut in accordance with a further embodiment the deflectable tip section of a catheter in accordance with the present invention.

A single puller wire 44, made of a non-metallic yarn such as Vectran® material, may be attached to the distal end of the catheter by threading the puller wire through one or more anchor holes 82*a-e* in center strut 80 so that the opposing ends of the puller wire, 44*a* and 44*b*, reside on opposing sides of the center strut as depicted in FIG. 8. Such anchor holes 82*a-e* in center strut 80 preferably have a diameter of 0.015 inch and are spaced apart by approximately 0.078 inch. Such anchor holes may be placed in the center strut 80 by laser cutting, punching and drilling. The number of holes on the strut, and the placement of the puller wires in one or more anchor holes 82*a-e* will alter the curve shape and allow for both symmetric and asymmetric curve designs. For creating a symmetric curve the opposing ends of the puller wires would exit the same anchor hole towards opposing sides of the strut. Means for changing curve shape can be controlled by the distance between anchor holes used for the opposing ends of the puller wire. When the end of each of the pull wires 44*a* and 44*b* are attached to opposing sides of the center strut 80, pulling pull wire 44*a* or 44*b* in the proximal direction will cause the distal end of the catheter 100 to deflect in-plane in the direction of the off-axis lumen in which the respective puller wire extends.

An alternate embodiment (not shown) uses two puller wires with metallic ferrules or plastic slugs to constrain the puller wires in their respective anchor hole located in the center strut. The puller wire would be threaded through the center strut on one side using the ferrule as a constraint from pulling completely through the anchor hole. An additional method for anchoring the puller wires is soldering, welding or using an adhesive to attach them to the center strut.

Figure 9:
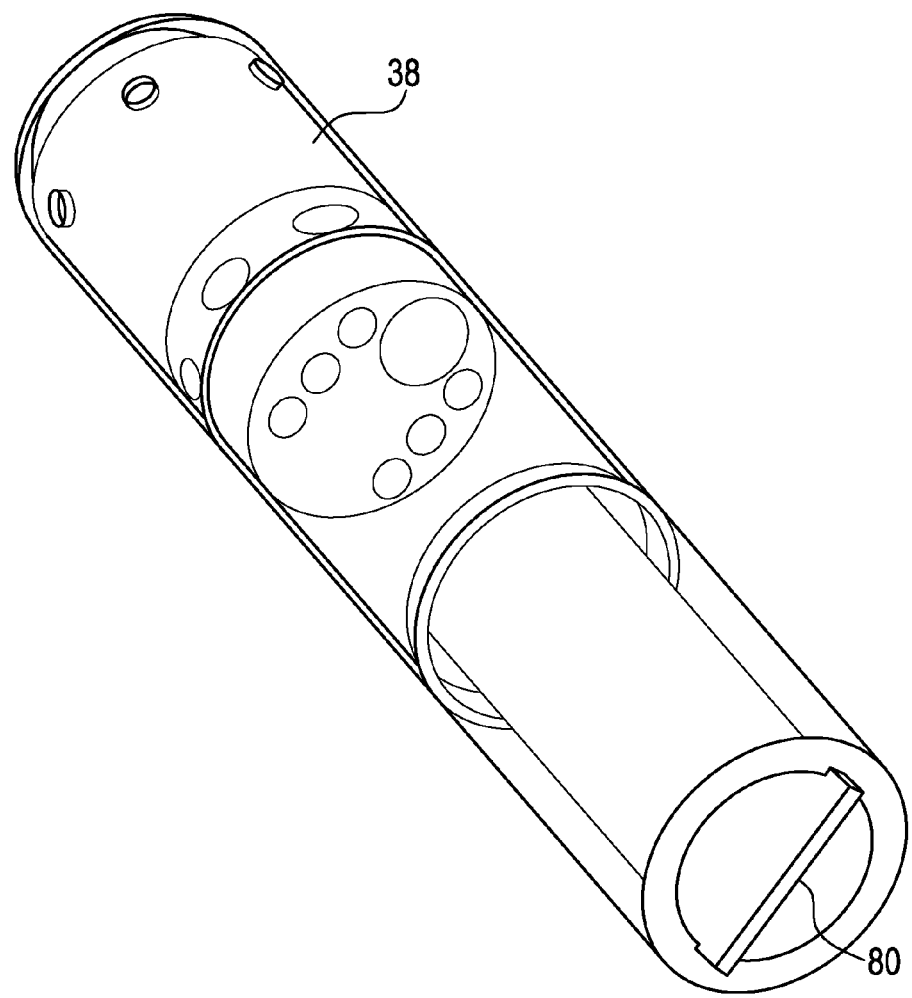
FIG. 9 is a perspective view of the device for manufacturing the deflectable tip section of a catheter in accordance with the present invention.
Figure 10:
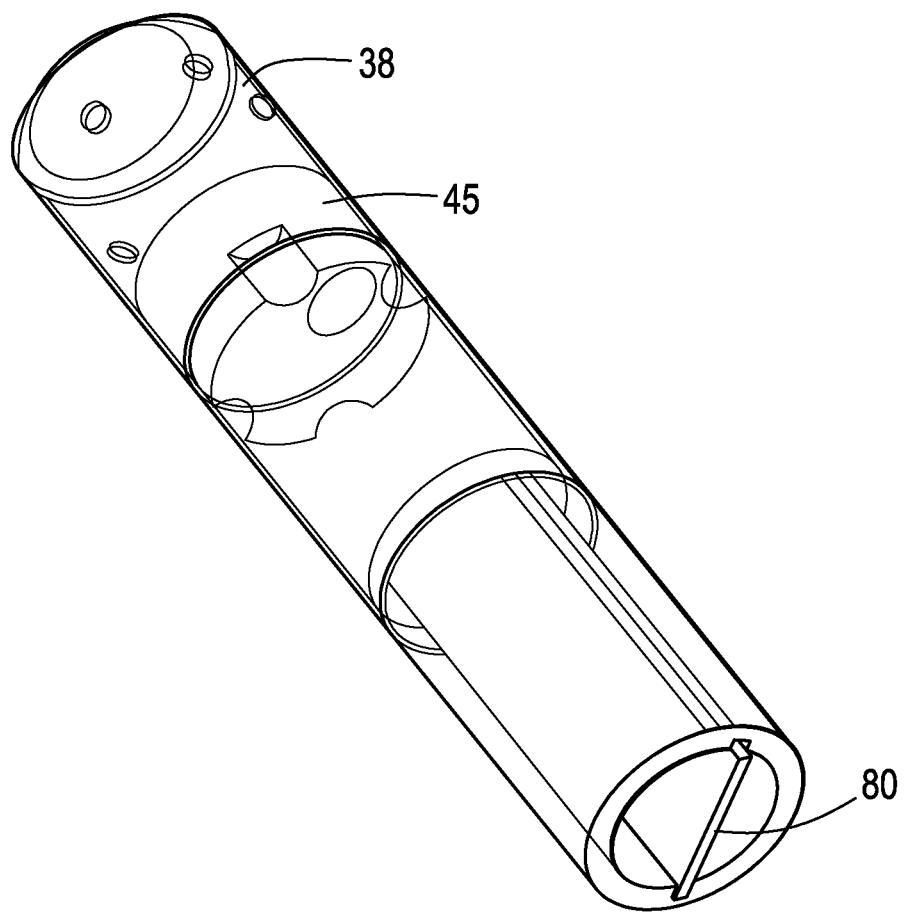
FIG. 10 is a perspective view of the distal tip of a deflectable catheter in accordance with the present invention.
Figure 11:
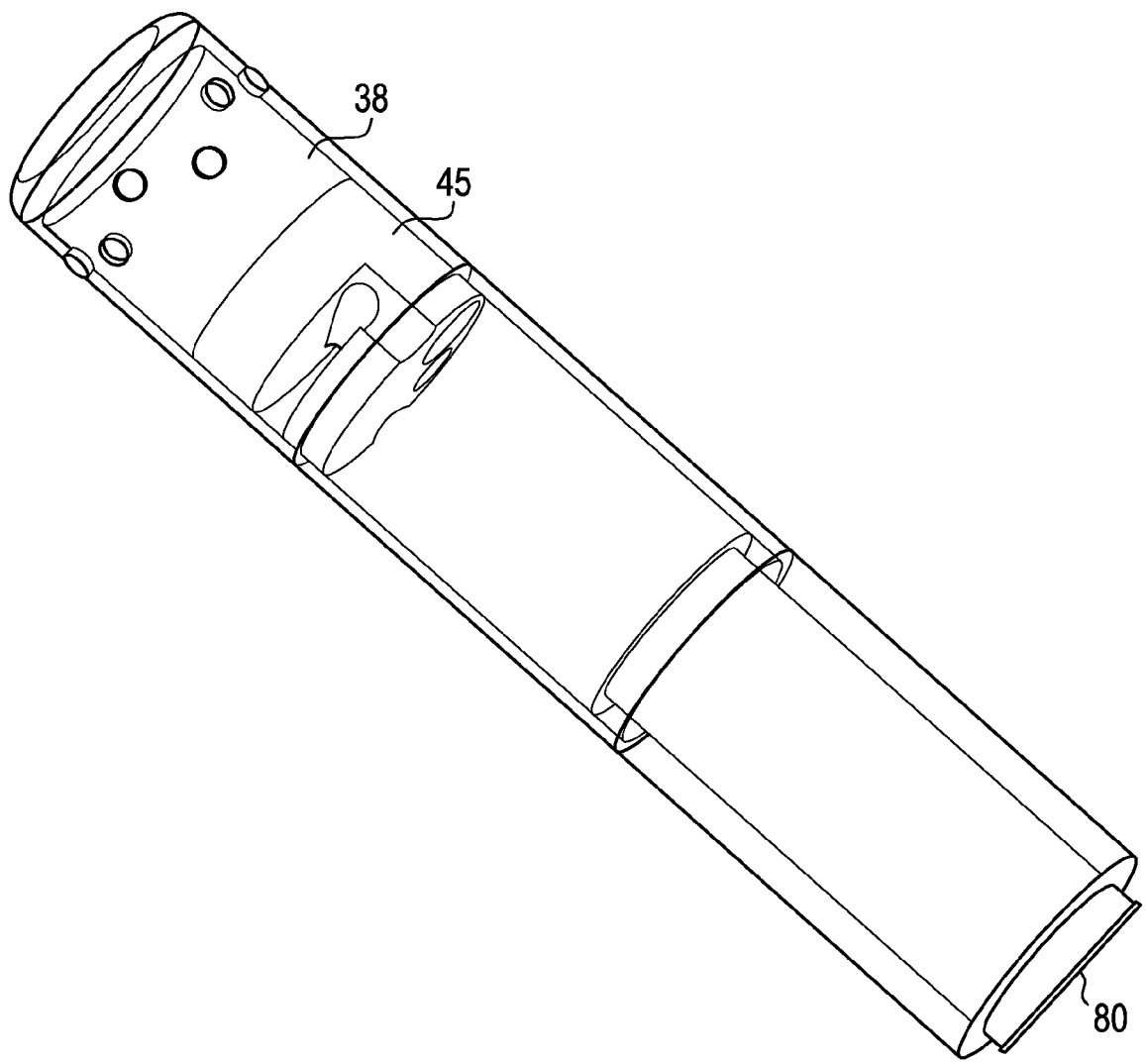
FIG. 11 is a perspective view of the distal tip of a deflectable catheter in accordance with the present invention.

Alternatively, the puller wires do not need to be attached to the center strut. A puller wire or puller wires could be attached to the tip dome or the distal end of the catheter's soft deflectable tip section. FIGS. 9-11 show multiple configurations of tip electrodes 38 that are adapted to receive a single puller wire 44. The single puller wire 44 connected to the tip electrode 38 provides bi-directional control. To achieve this, a single puller wire is threaded through the dome electrode with the opposite sides of the puller wire residing on opposite sides of the center strut. Deflection direction will correspond with the path of least resistance. Moreover, individually manipulating a puller wire will result in in-plane deflection in the direction of the off-axis lumen in which the respective puller wire extends. Such embodiment directly supports symmetric curve designs.

FIGS. 10 and 11 depict hollow tip electrodes 38 that are adapted to receive a plug 45 which is force fit into the hollow dome. Puller wire 44 is threaded through the plug. One or more puller wires may be anchored in this manner. The puller wire is constrained in place once the plug is appropriately placed in the tip electrode.

Figure 7B:
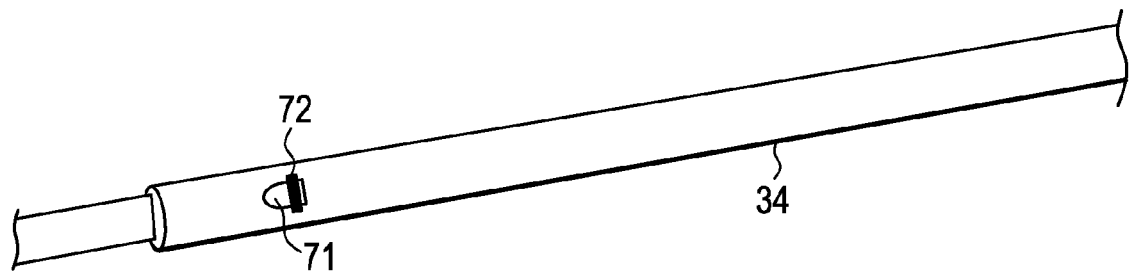
FIG. 7b is a perspective view of the distal section of a deflectable catheter in accordance with the present invention.

FIG. 7B depicts another embodiment of the distal tip section of the catheter 100 where the puller wires are attached to the side wall of the distal tip section 34 of catheter 100. A small hole 71 is drilled through the inner layer 62, braid layer 64 and outer layer 66 of the distal tip section. After the hole 71 is drilled, a grinder is used to lightly reduce the outer profile around the hole by removing approximately length=0.04" depth=0.013" of material. A stainless steel puller wire bar 72 is attached to the distal end of the puller wire 44 via crimping to a ferrule or other means of adhesion. When the puller wire 44 is brought through the anchor window the bar rests on the outer profile of the thermoplastic soft deflectable tip section. Polyurethane is used to pot over the puller wire bar 72 thereby rebuilding the original profile of the distal tip section 34. In this manner each puller wire may be anchored to the outer periphery of the catheter 100 at any location along the longitudinal axis of the distal tip section 34. It is possible to anchor multiple puller wires in this manner, each on opposing sides of the center strut. Changing the location of the anchoring location changes the deflection profile of the catheter.

The proximal end of the center strut 80 extends out of the proximal end of the soft deflectable tip portion. The proximal end of the center strut may be tapered so it can be readily placed within the proximal section 32 of the catheter helping to support the transition area. A sleeve preferably composed of PTFE may be placed over the tapered portion of the center strut constraining the puller wires and thereby preventing them from crossing. The sleeve is form fitting so it is tight around the center strut and wires but not so tight as to prevent the puller wires from readily moving in the longitudinal direction.

Figure 14:
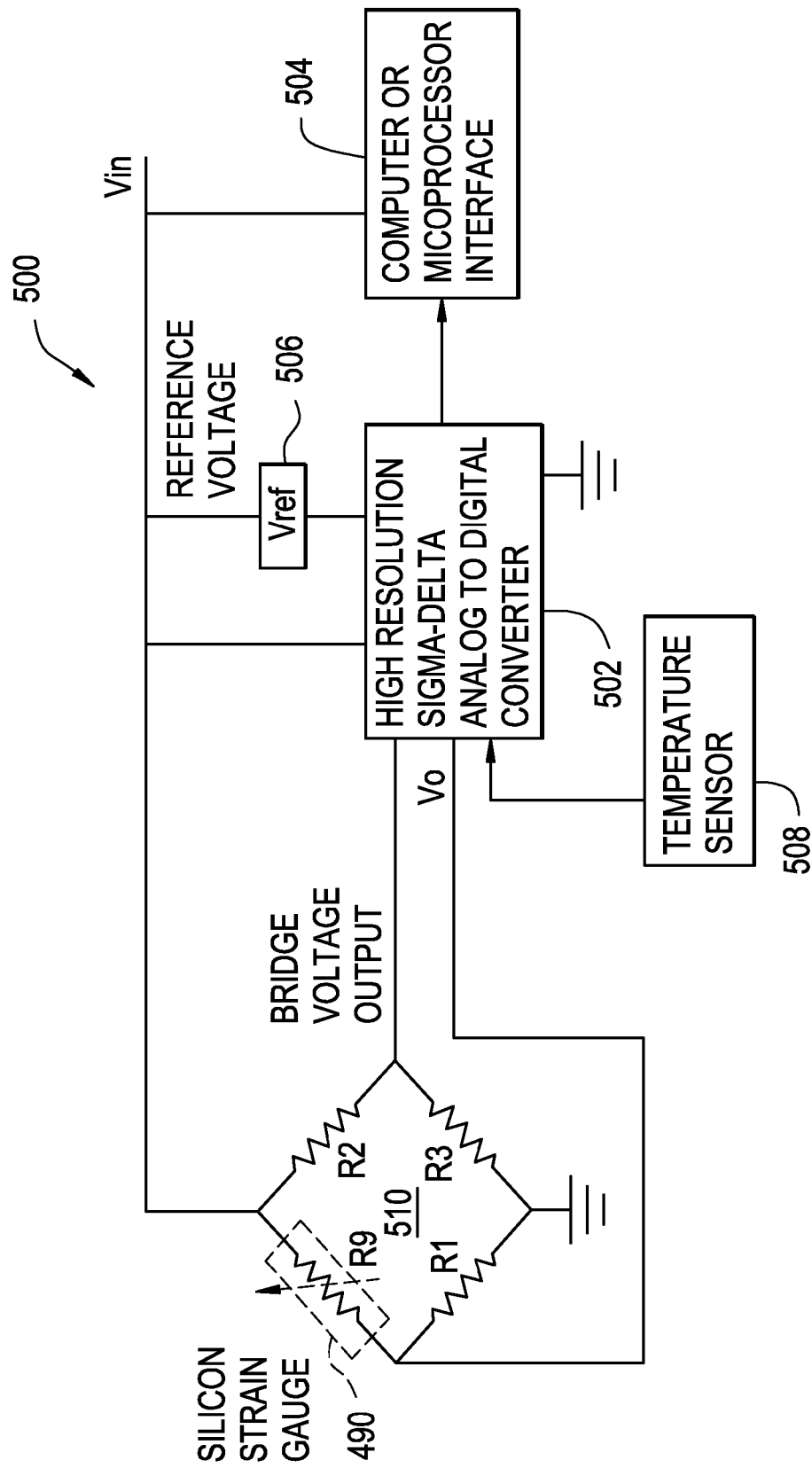
FIG. 14 depicts a schematic for the force measurement circuitry for use in a deflectable catheter having a silicon MEMS strain gage sensor in accordance with the present invention.

FIG. 14 depicts the schematic for a measurement circuit 500 for use with a force-sensing catheter having the silicon based strain gages. Measurement circuit 500 utilizes a high-resolution, sigma-delta analog-to-digital converter (ADC) 502 that includes differential inputs, programmable internal amplifiers, automatic zero calibration, high common-mode rejection, and digital noise filtering to aid in the strain sensor integration to accurately measure bridge circuit voltage output. Silicon strain gages 490 exhibit a high temperature coefficient of resistance (TCR) (temperature sensitivity) compared to constantan and other metal foils therefore temperature compensation circuitry and software algorithms (tables of temperature coefficients) are required as discussed below.

$$V_{OUT} = V_B \times (S \times S_0 \times (1 + S_1 \times (T-T_r)) + U_0 + U_1 \times (T-T_r)) \quad (1)$$

Equation (1) sets forth the formula for calculating the detected strain, where $V_{OUT}$ is the bridge voltage output, $V_B$ is the bridge excitation voltage, S is the applied sensor strain, $T_r$ is the reference temperature measured near the silicon strain sensor, $S_0$ is the strain gage sensitivity at reference temperature $T_r$, $S_1$ is the temperature coefficient of sensitivity (TCS), $U_0$ is the offset or unbalance of the bridge at $T_r$ with no strain applied, and $U_1$ is the offset temperature coefficient (OTC). OTC is the error band defined by the maximum deviation in offset voltage as the temperature is varied from 25° C. to any other temperature within the specified range. TCS corresponds to the slope of a tangent on the curve sensitivity versus temperature. Specifying this coefficient makes sense only if a linear or nearly linear relationship between temperature and sensitivity exists (Units: ppm/° C.). The semiconductor strain gages that would be utilized in this application have a linearity of ±0.25% to 600 u inch/inch and better than ±1.5% to 1500 u inch/inch.

Equation (1) uses first-order polynomials to model the silicon strain gage. To obtain higher measurement accuracy, higher-order polynomials, discrete interval linear techniques, or discrete interval second-order approximations with a table of coefficients may also be used. Digital calibration requires the ability to digitize $V_{OUT}$, $V_B$, and T, as well as a way to determine all the coefficients and perform the necessary calculations by utilizing a microcontroller or computer to calculate an accurate strain value.

The circuit shown in the FIG. 14 uses a single high-resolution ADC 502 to digitize $V_{OUT}$, the temperature near the silicon strain gage, and $V_B$ (bridge voltage). These measurements are then sent to a microprocessor or computer 504 (housed either in the handle of the catheter or in the ablation or navigation system to which the catheter is connected) where the strain is calculated using Equation (1). Microprocessor or computer 504 may be any type of general purpose computing device capable of providing mathematical computations by executing object code residing in an associated memory device. The bridge circuit is powered directly from the same power supply (not shown) as the ADC and the reference voltage Vr 506. A resistance temperature detector (RTD) or thermocouple comprising temperature sensor 508 measures the temperature near the silicon strain sensor for temperature compensation purposes. The strain sensor may also contain an integrated temperature sensor for temperature compensation purposes. The input multiplexer on the ADC 502 allows multiple silicon strain gage bridge voltages to be measured using the same ADC. To determine the temperature calibration coefficients, the catheter with internal silicon strain sensors is placed in a temperature controlled chamber or water bath and bridge voltage measurements are made at several different temperatures where the catheter will be used to determine the temperature calibration coefficients. These temperature calibration coefficients are then stored in a memory device associated with the catheter such as an EEPORM in the handle 36 of the device for use by the microprocessor 504.

Because of its outstanding sensitivity, the Wheatstone bridge circuit 510 is used for static strain measurement. Ideally, the strain gage is the only resistor in the circuit that varies and the bridge is considered balanced when R1/R2=Rg/R3 and, therefore, VOUT equals zero. When the bridge is set up so that Rg is the only active strain gage, a small change in Rg will throw the bridge out of balance resulting in an output voltage from the bridge.

For effective temperature compensation in metal foil strain gages 90 with long lead wires as in a catheter tip force-sensing application, a three-wire connection to the strain gage can be utilized as shown in FIG. 15. One-half of the lead wire resistance (½RL) is applied to the adjacent side of the Wheatstone bridge 510 to compensate the resistive components of the two leads affected by a similar temperature change and thus the bridge is free from any temperature effects from the long lead wires leading from the circuit to the location of the metal foil strain gage near the distal tip of the catheter. The temperature effect of the third lead wire connected to the amplifier can be ignored since the amplifier provides a high impedance input connection. With the three-wire system each lead wire must be of the same material, wire gage and length for proper temperature compensation purposes. Temperature effects on gage resistance and gage factor may not require compensation since most metallic gage alloys exhibit a nearly linear gage factor variation with temperature over a broad range which is less than ±1% within ±100° C. temperature range. Each strain gage wire material has its characteristic gage factor, resistance, temperature coefficient of gage factor, thermal coefficient of resistivity, and stability. Materials that may be used for strain gage construction include constantan, nichrome, platinum alloys, isoelastic (nickel-iron alloy), and karma-type alloy wires (nickel-chrome alloy). To double the bridge output for the same strain it may be useful to connect gages that are on opposite sides of a beam, one in compression and the other in tension.

A high-resolution analog-to-digital converter (ADC) 502 that includes differential inputs, programmable internal amplifiers, automatic zero calibration, high common-mode rejection, and digital noise filtering to aid in the strain sensor integration and to accurately measure bridge circuit voltage output. The output of the ADC 502 is communicated to the microprocessor 504 which perform the calculation set forth above to determine the strain.

In the elastic region of a stress-strain curve, the stress is linearly proportional to strain. The catheter tip is used in the elastic region so the tip is not permanently deformed, as this would cause the strain sensors not return to zero strain since the material that they are bonded would have yielded. Since the catheter is used in the linear region of the stress strain curve, the strain value is directly proportional and can be converted to the stress on the strut member in multiple orientations. The catheter tip has three different types of stresses acting upon it: Bending moment induced stress, torsional stress and shear stress which may be negligible compared to the other two stress components. By calibrating each catheter with different three-dimensional tip force vectors, the tip forces (grams) can be determined based upon the strain value from each strain gage and their corresponding placement orientation with respect to the strut.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A force-sensing catheter having a longitudinal axis for use in a vessel comprising:
    an elongate tubular member having a proximal end and a distal end, the distal end including a deflectable tip portion terminating in a distal tip, the elongate tubular member having a central lumen disposed through the proximal end and two half-cylindrical lumens in the deflectable tip portion;
    a tip electrode disposed at the distal tip of the deflectable tip portion;
    a center strut having a rectangular beam section along the longitudinal axis extending from near the proximal end of the tip electrode through the deflectable tip portion of the elongate tubular member and having a first longitudinal edge and a second longitudinal edge and a first side and a second side wherein the width of the first side and the second side are greater than the width of the first longitudinal edge and the second longitudinal edge respectively;
    wherein the center strut is bonded to the elongate tubular member substantially along entire length of the first longitudinal edge and the second longitudinal edge to form the two half-cylindrical lumen and create an inseparable composite structure from the center strut and the elongate tubular member; and,
    at least one strain gage, the at least one strain gage affixed to only the first side of the second side of the center strut, the at least one strain gage oriented and configured to detect a bending strain or torsional strain in the center strut for measuring force near the distal end of the tubular member.

2. The force-sensing catheter of claim 1 wherein a first strain gage and a second strain gage each having a strain measuring component are affixed to either the first side or the second side of the center strut with the strain measuring component of the first strain gage perpendicular to the strain measuring component of the second strain gage and the strain measuring component of each at a forty-five degree angle to the longitudinal axis of the catheter for measuring torsional strain on the distal tip of the catheter.

3. The force-sensing catheter of claim 1 wherein the strain gage having a strain measuring component is affixed to either the first side or the second side of the center strut so that the strain measuring component is axially aligned with the longitudinal axis of the catheter for measuring bending strain on the distal tip of the catheter.

4. The force-sensing catheter of claim 1 wherein a first strain gage and a second strain gage each having a strain measuring component are affixed to either the first side or the second side of the center strut with the strain measuring component of the first strain gage perpendicular to the strain measuring component of the second strain gage and the strain measuring component of each at a forty-five degree angle to the longitudinal axis of the catheter for measuring torsional strain on the distal tip of the catheter and a third strain gage having a strain measuring component is affixed to either the first side or the second side of the center strut so that the strain measuring component is axially aligned with the longitudinal axis of the catheter for measuring bending strain on the distal tip of the catheter.

5. The force-sensing catheter of claim 1 wherein the strain gage is a semiconductor strain gage.

6. The force-sensing catheter of claim 5 wherein the semiconductor strain gage is silicon based.

7. The force-sensing catheter of claim 5 wherein a table of offset temperature coefficients is stored in a memory device associated with the catheter for use in compensating for variations in sensed strain due to changes in the temperature of the environment in which the catheter is used.

8. The force-sensing catheter of claim 1 wherein the strain gage is a metallic foil strain gage.

9. The force-sensing catheter of claim 2 wherein the width of the center strut is narrowed parallel to where the first and second strain gages are affixed in order to amplify the torsional strain.

10. The force-sensing catheter of claim 3 further comprising at least one slot cut into the center strut near the strain gage, the slot configured to amplify the bending strain.

11. The force-sensing catheter of claim 1 wherein the center strut has been thermally bonded to the elongate tubular member substantially along the entire length of the center strut.

12. The force-sensing catheter of claim 1 further comprising a pull wire, having a proximal end and a distal end, for causing the deflectable distal portion of the elongate tubular member to deflect wherein the proximal end of the pull wire is attached to a control handle at the distal end of the catheter.

13. The force-sensing catheter of claim 12 wherein the distal end of the pull wire is attached to the tip electrode.

14. The force-sensing catheter of claim 1 further comprising a first pull wire and a second pull wire, each having a proximal end and a distal end, wherein the proximal end of the first and second pull wires are attached to a control handle and the distal end of the first pull wire is attached to the first side of the center strut and the distal end of the second pull wire is attached to the second side of the center strut.

15. The force-sensing catheter of claim 14 wherein the center strut comprises at least one anchor hole for attachment of the distal ends of the first and second pull wires.

16. The force-sensing catheter of claim 14 wherein the center strut comprises a plurality of anchor holes longitudinally spaced along the length of the center strut for attachment of the distal end of the first and second pull wires.

17. The force-sensing catheter of claim 16 wherein the plurality of anchor holes are spaced from adjacent anchor holes by approximately 0.078 inch.

18. The force-sensing catheter of claim 16 wherein the anchor holes are approximately 0.015 inch in diameter.

19. The force-sensing catheter of claim 1 further comprising a first pull wire and a second pull wire each having a proximal end and a distal end, wherein the proximal ends of the first and second pull wires are attached to a control handle and the distal ends of the first and second pull wires are attached to the tip electrode.

20. The force-sensing catheter of claim 19 wherein the tip electrode is comprised of a hollow portion and a plug and the distal ends of the first and second pull wires are attached to the plug prior to insertion in the hollow portion.

21. The force-sensing catheter of claim 1 further comprising a temperature sensor.

22. The force-sensing catheter of claim 21 wherein the temperature sensor is configured to provide an indication of the temperature of the tip of the catheter for use in temperature compensation of the output of the strain gage.

23. The catheter of claim 1 further comprising a location sensor.

24. The catheter of claim 1 wherein the tip electrode has irrigation ports and the catheter further comprises an irrigation lumen in communication with the irrigation ports.

25. The catheter of claim 1 further comprising a first pull wire and a second pull wire each having a proximal end and a distal end, wherein the proximal ends of the first and second pull wires are attached to a control handle and the distal ends of the first and second pull wires are attached to anchors and are threaded through first and second holes in the tubular member.

26. The catheter of claim 1 wherein the tubular member has an inner layer, a braided layer and an outer layer and wherein the first longitudinal edge and the second longitudinal edge of the center strut is thermally bonded to the inner layer.

27. The catheter of claim 1 wherein the center strut has been roughened along the first longitudinal edge and the second longitudinal edge to improve bonding with the tubular member.

28. The catheter of claim 1 further comprising a molded coupling adapted to receive the proximal end portion of the tip electrode.

29. The catheter of claim 28 wherein the distal end of the center strut comprises at least one snap-fit notch and the molded coupling further comprises at least one snap-fit wedge adapted to receive the snap-fit notch.

30. The catheter of claim 28 wherein the molded coupling further comprises at least one slot adapted to receive at least one of the first or second longitudinal edges of the distal portion of the center strut.

31. A catheter for use in a vessel comprising:
an elongate tubular member having a proximal end and a distal end, the distal end including a deflectable tip portion terminating in a distal tip, the elongate tubular member having a central lumen disposed through the proximal end and two half-cylindrical lumens in the deflectable tip portion;
a tip electrode disposed at the distal tip of the deflectable tip portion;
a center strut having a rectangular beam section extending from near the proximal end of the tip electrode through the deflectable tip portion of the elongate tubular member and having a first longitudinal edge and a second longitudinal edge and a first side and a second side;
a molded coupling having a distal portion adapted to receive a portion of the proximal end of the tip electrode and having a proximal portion having at least one slot adapted to receive the distal end of at least one of the first or second longitudinal edges of the center strut, the molded coupling defining a quick assembly mechanism;
wherein the center strut is bonded to the elongate tubular member substantially along entire length of the first longitudinal edge and the second longitudinal edge to form the two half-cylindrical lumens and create an inseparable composite structure of the center strut and the elongate tubular member and,
at least one strain gage, the at least one strain gage affixed to only one of the first side and/or the second side of the center strut, the at least one strain gage oriented and configured to detect the bending strain or torsional strain in the center strut for measuring force near the distal end of the tubular member.

32. The catheter of claim 31 wherein the distal end of the center strut comprises at least one snap-fit notch and the molded coupling further comprises at least one snap-fit wedge adapted to receive the snap-fit notch.

33. The force-sensing catheter of claim 31 wherein a first strain gage and a second strain gage each having a strain measuring component affixed to either the first side and/or the second side of the center strut with the strain measuring component of the first strain gage perpendicular to the strain measuring component of the second strain gage and the strain measuring component of each at a forty-five degree angle to the longitudinal axis of the catheter for measuring torsional strain on the distal tip of the catheter.

34. The force-sensing catheter of claim 31 wherein the strain gage having a strain measuring component is affixed to either the first side or the second side of the center strut so that the strain measuring component is axially aligned with the longitudinal axis of the catheter for measuring bending strain on the distal tip of the catheter.

35. The force-sensing catheter of claim 31 wherein a first strain gage and a second strain gage each having a strain measuring component are affixed to either the first side or the second side of the center strut with the strain measuring component of the first strain gage perpendicular to the strain measuring component of the second strain gage and the strain measuring component of each at a forty-five degree angle to the longitudinal axis of the catheter for measuring torsional strain on the distal tip of the catheter and a third strain gage having a strain measuring component is affixed to either the first side or the second side of the center strut so that the strain measuring component is axially aligned with the longitudinal axis of the catheter for measuring bending strain on the distal tip of the catheter.

36. The force-sensing catheter of claim 1 wherein the output of the strain gage is used to calculated the sensed force in accordance with the following equation:

$$V_{OUT} = V_B \times (S \times S_0 \times (1 + S_1 \times (T - T_r)) + U_0 + U_1 \times (T - T_r))$$

where $V_{OUT}$ is the bridge voltage output, $V_B$ is the bridge excitation voltage, S is the applied sensor strain, $T_r$ is the reference temperature measured near the silicon strain sensor, $S_0$ is the strain gage sensitivity at reference temperature $T_r$, $S_1$ is the temperature coefficient of sensitivity (TCS), $U_0$ is the offset or unbalance of the bridge at $T_r$ with no strain applied, and $U_1$ is the offset temperature coefficient (OTC).

* * * * *